(12) United States Patent
Nakajima et al.

(10) Patent No.: US 10,437,036 B2
(45) Date of Patent: Oct. 8, 2019

(54) ANALYSIS APPARATUS

(71) Applicant: ARKRAY, Inc., Kyoto-shi, Kyoto (JP)

(72) Inventors: Shinya Nakajima, Kyoto (JP); Shigeki Masuda, Kyoto (JP); Kenji Nakanishi, Kyoto (JP); Yukio Watanabe, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 16/144,812

(22) Filed: Sep. 27, 2018

(65) Prior Publication Data

US 2019/0101742 A1    Apr. 4, 2019

(30) Foreign Application Priority Data

Oct. 2, 2017   (JP) ................................ 2017-192652
Aug. 15, 2018  (JP) ................................ 2018-152902

(51) Int. Cl.
*G02B 21/36* (2006.01)
*G02B 21/18* (2006.01)
(Continued)

(52) U.S. Cl.
CPC ......... *G02B 21/365* (2013.01); *G01N 15/147* (2013.01); *G01N 15/1434* (2013.01);
(Continued)

(58) Field of Classification Search
CPC ............. G01N 15/147; G01N 21/6428; G01N 2015/1006; G01N 21/6458; G01N 15/1434; G01N 15/1459; G01N 15/1436; G01N 15/1475; G01N 2015/144; G01N 2015/1452; G01N 33/5091; G01N 2015/1472; G01N 2021/6439; G01N 2021/6441; G01N 21/64; G01N 21/645; G01N 15/1404; G01N 15/1484;
(Continued)

(56) References Cited

U.S. PATENT DOCUMENTS 6,153,873 A  * 11/2000  Wolf .................. G01N 15/0205
                                                     250/208.1
2002/0071121 A1* 6/2002  Ortyn .................... C07K 1/047
                                                     356/419
(Continued)

FOREIGN PATENT DOCUMENTS

DE   102014017552 A1   4/2016
JP       4948647 B2    6/2012

OTHER PUBLICATIONS

Extended European Search Report issued by the European Patent Office dated Mar. 15, 2019, which corresponds to EP18198344.6-1001 and is related to U.S. Appl. No. 16/144,812.

*Primary Examiner* — Michael P Stafira
(74) *Attorney, Agent, or Firm* — Studebaker & Brackett PC

(57) ABSTRACT

A plurality of images of a sample are simultaneously captured at different focal lengths by a plurality of cameras. An analysis apparatus includes: a branch section configured to cause light passing through the sample containing a material component to branch off into a plurality of optical paths; a plurality of imaging devices for simultaneously capturing images of the sample in a flow path at different focal points by using the light caused to branch off into the plurality of optical paths; and a controller configured to process the captured images.

11 Claims, 13 Drawing Sheets

(51) Int. Cl.
*G02B 21/06* (2006.01)
*G01N 33/493* (2006.01)
*G01N 21/05* (2006.01)
*G01N 15/14* (2006.01)
*G01N 21/17* (2006.01)
*G01N 15/10* (2006.01)

(52) U.S. Cl.
CPC ........... *G01N 21/05* (2013.01); *G01N 33/493* (2013.01); *G02B 21/06* (2013.01); *G02B 21/18* (2013.01); *G01N 2015/1006* (2013.01); *G01N 2015/1445* (2013.01); *G01N 2021/052* (2013.01); *G01N 2021/1772* (2013.01)

(58) Field of Classification Search
CPC ... G01N 2015/0065; G01N 2015/1415; G01N 2015/1443; G01N 2015/1479; G01N 2015/1495; G01N 21/6456; G01N 33/50; G01N 2015/1497; G01N 2021/6419; G01N 21/6486; G01N 2015/1486; G01N 2015/0294; G01N 2015/1447; G01N 2015/1488; G01N 2021/052; G01N 2021/058; G01N 2035/1032; G01N 21/45; G01N 21/85; G01N 33/5005; G01N 33/505; G01N 2021/6421; G01N 2035/00346; G01N 21/253; G01N 21/6452; G01N 35/025; G01N 35/1002; G01N 15/06; G01N 15/1429; G01N 15/1463; G01N 1/38; G01N 2015/0693; G01N 2021/458; G01N 2035/0443; G01N 2035/0444; G01N 2035/0446; G01N 2035/0455; G01N 21/51; G01N 2201/061; G01N 2201/105; G01N 2201/12; G01N 33/6875; G01N 15/1012; G01N 2015/1018; G01N 2015/1025; G01N 2015/1075; G01N 2035/00356; G01N 2035/00752; G01N 2035/0091; G01N 21/13; G01N 2201/025; G01N 33/5094; G01N 33/54366; G01N 35/04; G01N 35/1095; G01N 15/14; G01N 2021/6417; G01N 21/031; G01N 21/05; G01N 21/53; G01N 21/648; G01N 33/574; G01N 33/57492; G01N 15/0205; G01N 15/1425; G01N 1/2813; G01N 1/30; G01N 1/312; G01N 2015/1445; G01N 2015/1465; G01N 2015/1477; G01N 2021/1727; G01N 2021/6471; G01N 2035/00158; G01N 21/1717; G01N 21/274; G01N 21/6408; G01N 21/6445; G01N 21/6489; G01N 21/8483; G01N 21/8806; G01N 2201/0221; G01N 2201/06113; G01N 2201/1296; G01N 33/4833; G01N 33/491; G01N 33/543; G01N 33/54346; G01N 33/54373; G01N 33/54393; G01N 33/551; G01N 33/56972; G01N 33/57407; G01N 33/6854; G01N 35/00009; G01N 35/00029; G01N 35/00069; G01N 35/00584; G01N 35/10; G02B 7/28; G02B 27/0012; G02B 21/04; G02B 21/361; G02B 27/0025; G02B 27/1013; G02B 27/144; G02B 27/145; G02B 27/148; G02B 6/26; G02B 6/29365; G02B 21/00; G02B 21/244; G02B 27/126; G02B 21/34; G02B 21/125; G02B 21/16; G02B 21/26; G02B 21/0008; G02B 21/0076; G02B 21/008; G02B 21/0088; G02B 21/0096; G02B 21/06; G02B 21/24; G02B 21/245; G02B 21/28; G02B 21/32; G02B 21/36; G02B 21/362; G02B 27/0972; G02B 27/0994; G02B 5/001; G02B 5/32; G01J 3/2803; G01J 3/2823; G01J 3/4406; G01J 3/2889; G01J 3/36; G01J 3/28; G01B 11/24; G01B 9/02063; G01B 11/0675; G01B 11/2441; G01B 9/021

See application file for complete search history.

(56) References Cited

U.S. PATENT DOCUMENTS

| | | | | |
|---|---|---|---|---|
| 2004/0021868 A1* | 2/2004 | Ortyn | ................... | C12Q 1/6816 356/419 |
| 2005/0109950 A1* | 5/2005 | King | .................... | G01N 15/147 250/458.1 |
| 2005/0174572 A1* | 8/2005 | Czarnek | ............ | G01N 15/1404 356/246 |
| 2008/0317325 A1* | 12/2008 | Ortyn | ................... | G01N 15/147 382/133 |
| 2010/0157086 A1* | 6/2010 | Segale | ............... | G01N 21/6458 348/222.1 |
| 2010/0291588 A1* | 11/2010 | McDevitt | .......... | B01L 3/502715 435/7.2 |
| 2011/0002516 A1 | 1/2011 | Manri et al. | | |
| 2011/0090247 A1* | 4/2011 | Taki | .................... | G01N 15/1459 345/620 |
| 2013/0328918 A1* | 12/2013 | Okamura | .............. | G06T 3/0093 345/625 |
| 2014/0030729 A1* | 1/2014 | Basiji | ............... | G01N 33/57492 435/6.14 |
| 2014/0319376 A1* | 10/2014 | Pratt | ..................... | G01J 3/4406 250/458.1 |
| 2017/0315039 A1 | 11/2017 | Beil et al. | | |

* cited by examiner

ANALYSIS APPARATUS

CROSS REFERENCE TO RELATED APPLICATIONS

This application claims priority to Japanese Patent Application No. 2017-192652 filed on Oct. 2, 2017 and No. 2018-152902 filed on Aug. 15, 2018, the entire contents of which are incorporated by reference herein.

TECHNICAL FIELD

The present disclosure relates to an analysis apparatus.

BACKGROUND ART

In a test of collected urine, a sediment component (material component) in urine has hitherto been analyzed by a method that centrifuges the collected urine and directly observes particles in the urine by a microscope, but the analysis has been time consuming. Therefore, urine sediment analysis is becoming more automatized, and there is known a method that performs analysis of the sediment component (material component) in urine by imaging a urine sample that flows in a flow path provided in a flow cell formed by a transparent member and analyzing the captured image (see, e.g., Japanese Patent No. 4948647). A device described in Japanese Patent No. 4948647 has a review function that enables a user to display any image, revise automatic classification, and perform reclassification by visual confirmation.

PRIOR ART LITERATURE

Patent Literature

Patent Literature 1: Japanese Patent No. 4948647

SUMMARY

Technical Problem

The test of the sediment component in the urine includes an operation for (distinguishing the type of the sediment component in the urine and an operation for counting the number of the sediment components. In the distinguishing operation, a device that distinguishes the type of the sediment component in the urine extracts a feature amount from an image of the sediment component and distinguishes the type by performing pattern matching of the feature amount. When the type cannot be distinguished, a person distinguishes the type by visual confirmation by using a microscope. In the count operation, the sediment components are extracted from an image of a urine sample flowing through the flow cell and the number of the sediment components is counted.

In the distinguishing operation using the device, the type is distinguished by using an image of the sediment component in an image captured at a fixed focal length. When the image is out of focus, there have been cases where the feature amount cannot be appropriately extracted and the type cannot be appropriately distinguished. In that case, it has been inefficient to perform the distinguishing by visual confirmation by using the microscope.

On the other hand, in the count operation, the urine sample flowing through the flow cell is flowing with a predetermined thickness, and the sediment components are distributed in the thickness direction. The distribution range of the sediment components in the thickness direction is wider than the depth of field imaged by the device When the imaging is performed at a fixed focal length, there have been cases where the sediment components outside the range of the depth of field cannot be imaged and the count cannot be appropriately performed.

An object of the present disclosure is to provide an analysis apparatus that simultaneously captures a plurality of images of a sample at different focal lengths by a plurality of cameras in view of the abovementioned problems

Solution to Problem

An aspect of the present disclosure is an analysis apparatus, including: a flow cell including a flow path for a sample containing a material component; a branch section configured to cause light passing through the sample containing the material component to branch off into a plurality of optical paths; a plurality of imaging devices for simultaneously capturing images of the sample in the flow path at different focal points by using the light caused to branch off into the plurality of optical paths; and a controller configured to process the captured images

Advantageous Effect

According to the present disclosure, the accuracy in the analysis of the sample flowing through the flow cell can be enhanced by simultaneously capturing the plurality of images of the sample at different focal lengths by the plurality of cameras.

DESCRIPTION OF THE EMBODIMENT

Hereinbelow, with reference to the drawings, preferred embodiments of the present disclosure will be described. It should be noted that, however, unless otherwise specified expressly, the dimensions, materials, shapes, and relative arrangements of components described in these embodiments are not intended to limit the scope of the present disclosure to the dimensions, materials, shapes, and relative arrangements thereof. Material components in body fluid other than urine such as blood, cerebrospinal fluid, and serous fluid can be also analyzed as samples.

Embodiment

Figure 1:
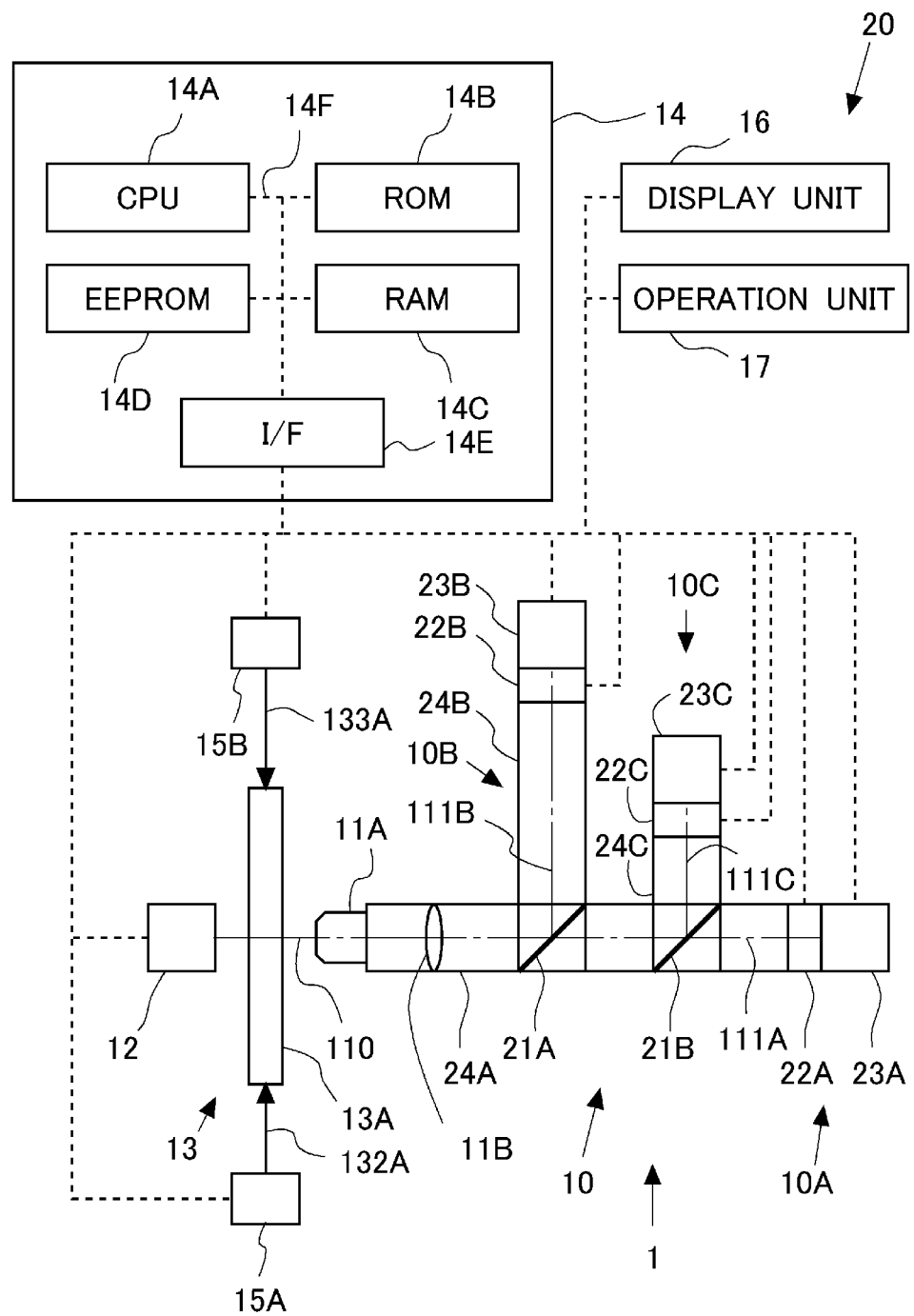
FIG. 1 is a view showing the schematic configuration of an analysis apparatus according to an embodiment.

FIG. 1 is a view showing the schematic configuration of an analysis apparatus 20 according to an embodiment. The analysis apparatus 20 includes an imaging unit 1. The imaging unit 1 images, e.g., urine as a sample. The analysis apparatus 20 performs analysis of, e.g., a material component (a solid component in the urine such as an erythrocyte, a leukocyte, a squamous cell, other epithelial cells, a cast, a crystal, and a *bacterium*) in the urine by analyzing the captured image. The analysis can include qualitative analysis and quantitative analysis. Note that the imaging unit 1 can also be applied to the analysis of the material component in a fluid sample other than urine such as, e.g., blood or body fluid.

The imaging unit 1 includes an objective lens 11A, a light source 12 for imaging, a flow cell unit 13, a first branch section 21A, a second branch section 21B, a first variable mechanism 22A, a second variable mechanism 22B, a third variable mechanism 22C, a first camera 23A, a second camera 23B, and a third camera 23C. In addition, the imaging unit 1 includes a first lens barrel 24A, a second lens barrel 24B, and a third lens barrel 24C, and the first branch section 21A and the second branch section 21B are accommodated in the first lens barrel 24A. The objective lens 11A is disposed on one end of the first lens barrel 24A, and the first camera 23A is disposed on the other end of the first lens barrel 24A. The second lens barrel 24B and the third lens barrel 24C are connected to the first lens barrel 24A in the order from the objective lens 11A side so that the central axes of the second lens barrel 24B and the third lens barrel 24C orthogonally intersect the first lens barrel 24A. The second camera 23B is disposed on an end portion of the second lens barrel 24B, and the third camera 23C is disposed on an end portion of the third lens barrel 24C.

Each of the first camera 23A, the second camera 23B, and the third camera 23C as imaging devices performs imaging by using an image sensor such as, e.g., a charge coupled device (COD) image sensor or a complementary metal oxide semiconductor (CMOS) image sensor. The first camera 23A, the second camera 23B, and the third camera 23C have the same performance capabilities, but those having different performance capabilities can also be used.

Hereinafter, the objective lens 11A, the first branch section 21A, the second branch section 21B, the first variable mechanism 22A, and the first camera 23A are collectively referred to as a first imaging section 10A, the objective lens 11A, the first branch section 21A, the second variable mechanism 22B, and the second camera 23B are collectively referred to as a second imaging section 10B, and the objective lens 11A, the first branch section 21A, the second branch section 21B, the third variable mechanism 22C, and the third camera 23C are collectively referred to as a third imaging section 10C.

There is an imaging lens 11B in the first lens barrel 24A on the objective lens 11A side than the first branch section 21A. The objective lens 11A, the imaging lens 11B, and the light source 12 are shared by the first imaging section 10A, the second imaging section 10B, and the third imaging section 10C. The first imaging section 10A, the second imaging section 10B, and the third imaging section 10C have the same depth of field, field of view, and magnification when the optical path lengths from the imaging lens 11B (the objective lens 11A when there is no imaging lens 11B) to the first camera 23A, the second camera 23B and the third camera 23C are the same.

Note that the first imaging section 10A, the second imaging section 10B, and the third imaging section 10C are hereinafter simply referred to as an imaging section 10 when no distinction is made therebetween. The first branch section 21A and the second branch section 21B are simply referred to as a branch section 21 when no distinction is made therebetween. The first variable mechanism 22A, the second variable mechanism 22B, and the third variable mechanism 22C are simply referred to as a variable mechanism 22 when no distinction is made therebetween. The first camera 23A, the second camera 23B, and the third camera 23C are simply referred to as a camera 23 when no distinction is made therebetween. The first lens barrel 24A, the second lens barrel 24B, and the third lens barrel 24C are simply referred to as a lens barrel 24 when no distinction is made therebetween.

The first branch section 21A and the second branch section 21B are beam splitters such as, e.g., half mirrors and causes light to branch off in two directions. The first branch section 21A and the second branch section 21B are disposed on an optical axis 110 of the objective lens 11A. The first branch section 21A causes light to branch off in two directions by transmitting a part of the light that has passed through the objective lens 11A and reflecting the remaining light. The first branch section 21A is disposed so that an optical axis 111B of the light reflected by the first branch section 21A matches with the central axis of the second lens barrel 24B. The light reflected by the first branch section 21A enters the imaging surface of the image sensor of the second camera 23B and is used for imaging in the second imaging section 10B by disposing the first branch section 21A as above.

The second branch section 21B further causes to the light to branch off in two directions by transmitting a part of the light transmitted by the first branch section 21A and reflecting the remaining light. The second branch section 21B is disposed so that an optical axis 111C of the light reflected by the second branch section 21B matches with the central axis of the third lens barrel 24C. The light transmitted by the second branch sect on 21B enters the imaging surface of the image sensor of the first camera 23A and as used for imaging in the first imaging section 10A by disposing the second branch section 21B as above. The light reflected by the second branch section 21B enters the imaging surface of the image sensor of the third camera 23C and is used for imaging in the third imaging section 10C.

The path of the light transmitted by the second branch section 21B and entering the first camera 23A is referred to as a first optical path, the path of the light reflected by the first branch section 21A and entering the second camera 23B is referred to as a second optical path, and the path of the light reflected by the second branch section 21B and entering the third camera 23C is referred to as a third optical path. The optical axis of the first optical path matches with the optical axis 110 of the objective lens 11A. In FIG. 1, the optical axis of the first optical path is denoted by 111A, the optical axis of the second optical path is denoted by 111B, and the optical axis of the third optical path is denoted by 111C. The optical axis of the first optical path, the optical axis of the second optical path, and the optical axis of the third optical path are simply referred to as an optical axis 111 when no distinction is made therebetween.

As shown in FIG. 1, the first camera 23A, the second camera 23B, the third camera 23C share the objective lens 11A and the imaging lens 11B, and hence the position (referred to as a center of the field of view) through which the optical axis 110 of the objective lens 11A passes with respect to an object is common to the plurality of cameras. Note that the optical path lengths between the imaging lens 11B and the imaging surfaces of the first camera 23A, the second camera 23B, and the third camera 23C are different from each other as described below. Therefore, the focal points of the first camera 23A, the second camera 23B, and the third camera 23C on the object side thereof are shifted from each other in the direction of the optical axis 110 of the objective lens 11A (see FIG. 6).

The analysis apparatus 20 is provided with a controller 14 serving as a control section. The controller 14 includes a CPU 14A, a ROM 14B, a RAM 14C, an EEPROM 14D, and an interface circuit 14E which are connected to each other using a bus 14F.

The central processing unit (CPU) 14A operates based on a program that is stored in the read only memory (ROM) 14B and is read by the random access memory (RAM) 14C, and controls the entire analysis apparatus 20. In the ROM 14B, the program and data for causing the CPU 14A to operate are stored. The RAM 14C provides a work area for the CPU 14A, and temporarily stores various pieces of data and various programs. The electrically erasable programmable read only memory (EEPROM) 14D stores various pieces of setting data. The interface circuit 14E controls communication between the CPU 14A and various circuits. Control lines of a display unit 16, an operation unit 17, the first variable mechanism 22A, the second variable mechanism 22B, the third variable mechanism 22C, the first camera 23A, the second camera 23B, the third camera 23C, the light source 12, a first pump 15A, and a second pump 15B are connected to the interface circuit 14E, and these devices are controlled by control signals from the controller 14. The first pump 15A supplies a sheath fluid to a flow cell 13A via a first supply pipe 132A, and the second pump 15B supplies a sample to the flow cell 13A via a second supply pipe 133A. The sheath fluid is a fluid for controlling the flow of the sample in the flow cell 13A, and a physiological saline solution is used in the case where the sample is, e.g., urine. Note that a solution other than the physiological saline solution may be used as the sheath fluid.

For example, a xenon lamp or a white LED can be employed for the light source 12, but the light source 12 is not limited thereto and other light sources can also be employed. The display unit 16 includes, e.g., a liquid crystal display (LCD) or a light-emitting diode, and is controlled by the CPU 14A to display, e.g., various information, test results, and images in which the material components are imaged. The operation unit 17 is an interface used when the user operates the analysis apparatus 20, and includes, e.g., a switch, a keyboard, and a mouse. The operation unit 17 supplies operation signals corresponding to the operation of the user to the CPU 14A.

The flow cell unit 13 includes a stage (not shown) on which the flow cell 13A through which the sample flows is fixedly disposed. The flow cell 13A may be removably mounted on the stage. The flow cell 13A is disposed between the light source 12 and the objective lens 11A.

Figure 2:
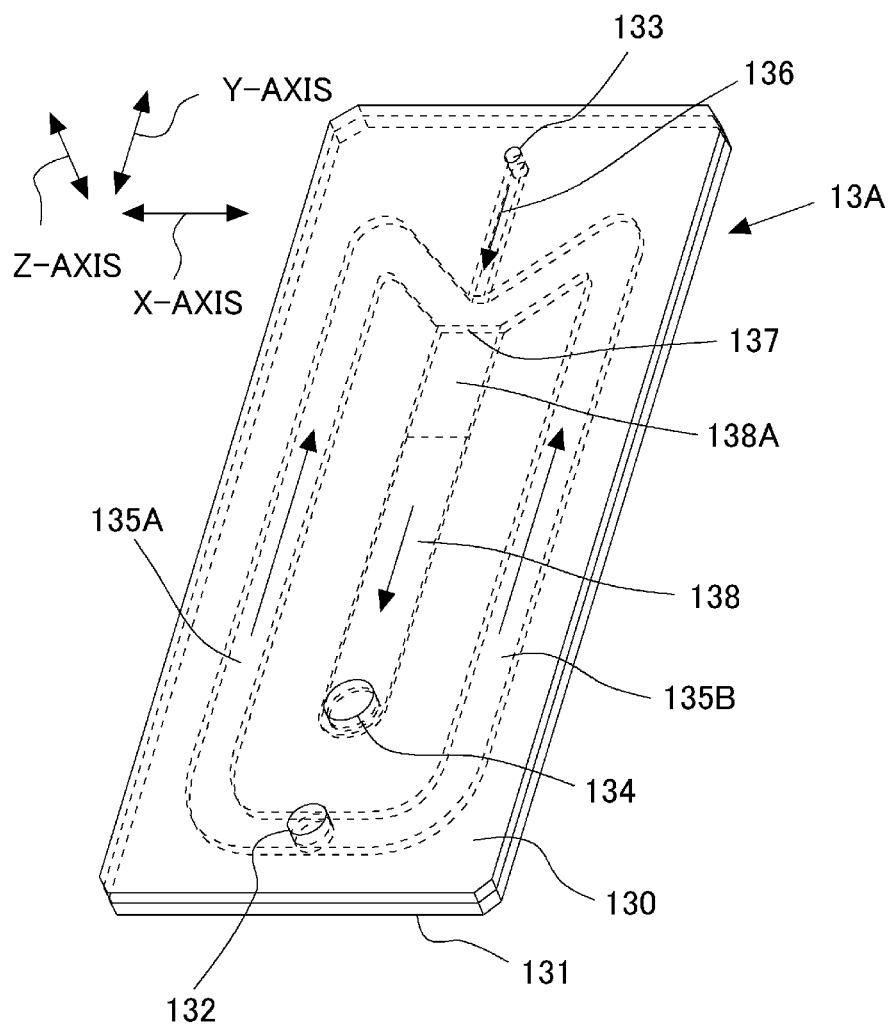
FIG. 2 is a view showing the schematic configuration of a flow cell.

FIG. 2 is a view showing the schematic configuration of the flow cell 13A. The flow cell 13A is formed by bonding a first plate 130 and a second plate 131 together (e.g., thermocompression bonding). FIG. 2 is a view in which the flow cell 13A is viewed from the side of the first plate 130. Note that it is assumed that the width direction of the flow cell 13A shown in FIG. 2 is an X-axis direction in a Cartesian coordinate system, the length direction thereof is a Y-axis direction, and the thickness direction thereof is a Z-axis direction. The sample to be imaged flows in the Y-axis direction in the flow cell 13A. The optical axis 110 of the objective lens 11A is disposed in the Z-axis direction.

As the material of the flow cell 13A, it is possible to use a material having visible light permeability of 90% or more such as, e.g., acrylic resin (PMMA), cycloolefin polymer (COP) polydimethylsiloxane (PDMS), polypropylene (PP), or quartz glass.

The first plate 130 is provided with a first supply port 132 for supplying the sheath fluid, a second supply port 133 for supplying the sample, and a discharge port 134 for discharging the sheath fluid and the sample. Each of the first supply port 132, the second supply port 133, and the discharge port 134 passes through the first plate 130. The first supply port 132 is provided at one end side in the longitudinal direction of the first plate 130, the second supply port 133 is provided at the other end side in the longitudinal direction of the first plate 130, and the discharge port 134 is provided between the first supply port 132 and the second supply port 133 in the longitudinal direction of the first plate 130.

The first supply port 132 the second supply port 133, and the discharge port 134 are caused to communicate with each other using flow paths 135A, 135B, 136, and 138. Each of the flow paths 135A, 135B, 136, and 138 is formed so as to be depressed from the surface of the bonding surface side of the first plate 130 such that the cross section thereof is rectangular. In addition, the cross section of each of the flow paths 135A, 135B, 136, and 138 is formed so as to be larger in a width direction (the X-axis direction in FIG. 2) than in a depth direction (the Z-axis direction in FIG. 2). When the first plate 130 and the second plate 131 are bonded together, the second plate 131 serves as a wall material that forms the flow paths 135A, 135B, 136, and 138.

The first flow path 135A and the second flow path 135B are connected to the first supply port 132. The first flow path 135A and the second flow path 135B extend in clockwise and counterclockwise directions toward the side of the second supply port 133 along the outer edge of the first plate 130, and join together at a joining section 137. In addition, the third flow path 136 is connected to the second supply port 133, and joins the first flow path 135A and the second flow path 135B at the joining section 137. The joining section 137 is connected to the discharge port 134 via the fourth flow path 138. The fourth flow path 138 is formed with a tapered section 138A that is formed into a tapered shape in which the depth of the fourth flow path 138 (the length in the thickness direction of the first plate 130 (Z-axis direction)) is gradually reduced toward the discharge port 134 from the joining section 137. The tapered section 138A is inclined, e.g., 2° to 8°.

The first supply pipe 132A shown in FIG. 1 is connected to the first supply port 132, the second supply pipe 133A shown in FIG. 1 is connected to the second supply port 133, and a discharge pipe (not shown) is connected to the discharge port 134. The sheath fluid supplied to the first supply port 132 from the first supply pipe 132A flows in the first flow path 135A and the second flow path 1350. The sample supplied to the second supply port 133 from the second supply pipe 133A flows in the third flow path 136. Subsequently, the sheath fluid and the sample join together at the joining section 137, flow in the fourth flow path 138, and are discharged to the discharge pipe from the discharge port 134.

Figure 3:
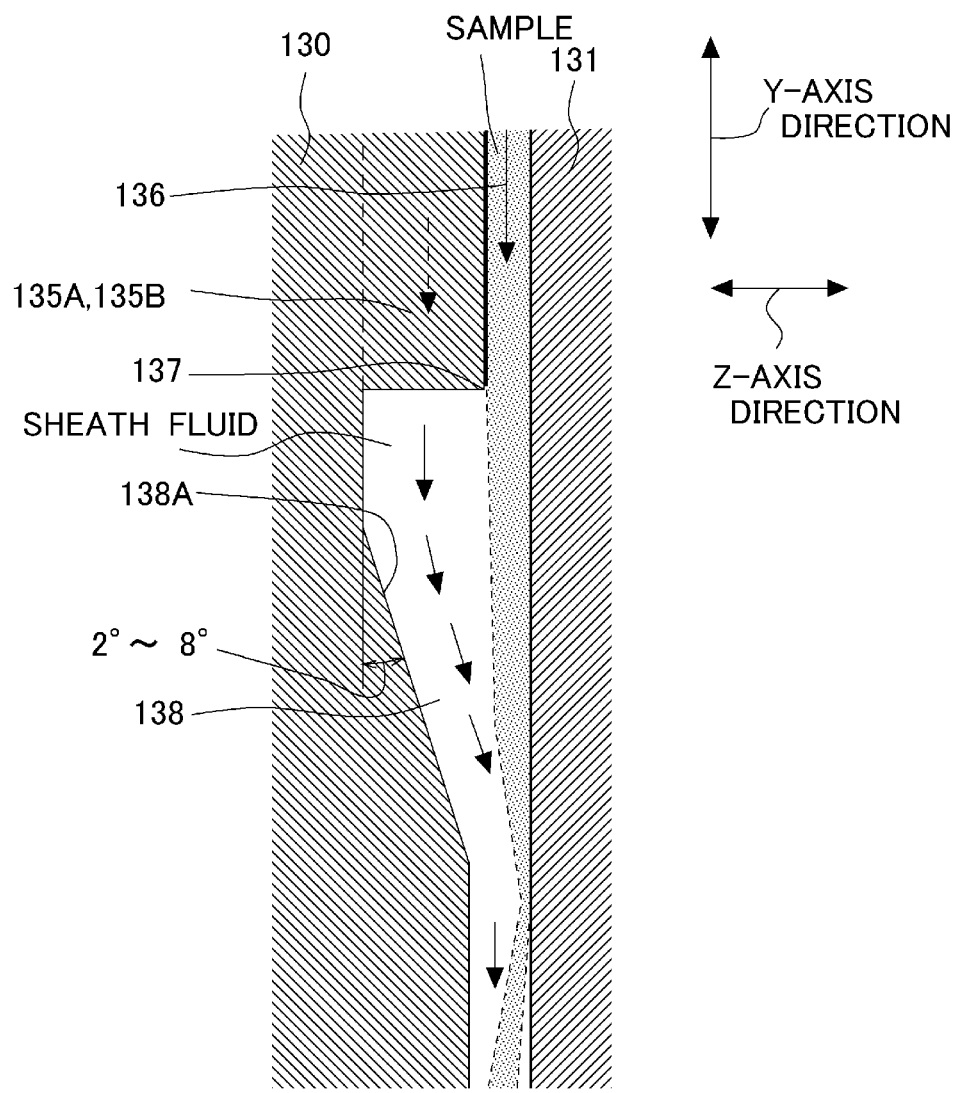
FIG. 3 is a cross-sectional view in a Y-axis direction showing the schematic configuration in the vicinity of a joining section and a tapered section.

FIG. 3 is a cross-sectional view in the Y-axis direction showing the schematic configuration in the vicinity of the joining section 137 and the tapered section 138A. In the joining section 137, the third flow path 136 is disposed so as to be close to the second plate 131, and the sample flows along the second plate 131 in the joining section 137.

Figure 4:
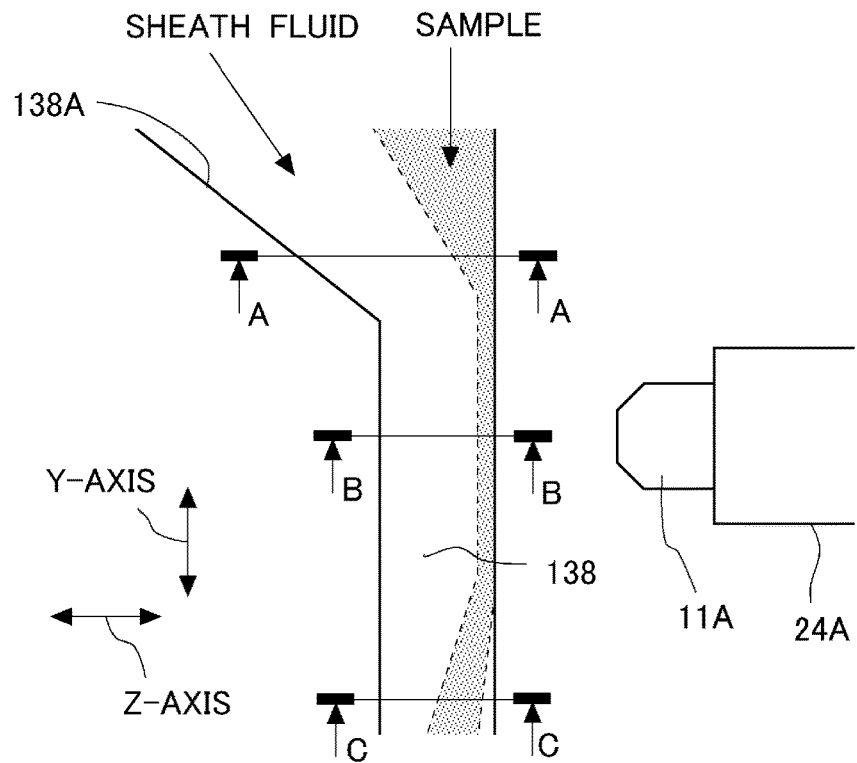
FIG. 4 is a view showing the distributions of a sheath fluid and a sample that flow in a fourth flow path.
Figure 4:
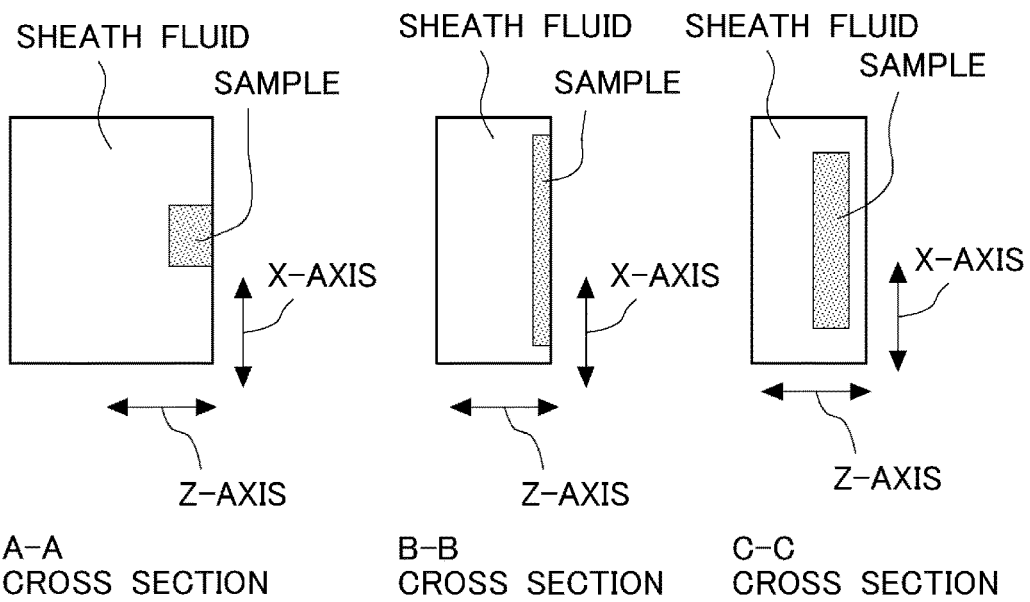

FIG. 4 is view showing the distributions of the sheath fluid and the sample that flow in the fourth flow path 138. After the sheath fluid and the sample are supplied separately from the upper side in FIG. 4, the sheath fluid and the sample join together at the joining section 137. Immediately after the joining of the sheath fluid and the sample at the joining section 137, the sample in the sheath fluid is concentrated on a relatively narrow area on the side of the wall surface of the second plate 131 (see an A-A cross section in FIG. 4). Thereafter, when the sample flows in the tapered section 138A, the sample is pushed by the sheath fluid, and spreads flatly along the wall surface in the vicinity of the wall surface of the second plate 131 (see a B-B cross section in FIG. 4). When the sample further flows, the sample moves away from the wall surface of the second plate 131 due to the tubular pinch effect, and is lifted toward the direction of center of the fourth flow path 138 (see a C-C cross section in FIG. 4).

The distribution of a material component is influenced by the distribution of a sample fluid in the sheath fluid. By performing imaging at a position that allows imaging of more material components, it is possible to increase accuracy in the analysis of the material component. As shown in the cross-sectional views in FIG. 4, in the flow cell 13A, the flow of the sample changes depending on the position in the Y-axis direction. At the potion in the C-C cross section in FIG. 4, the width of the sample in the Z-axis direction is larger than the width thereof at the position in the B-B cross section. At the position in the C-C cross section in FIG. 4, the material components in the sample are distributed so as to spread in the Z-axis direction, and hence the position in the C-C cross section is not suitable for imaging of the material components.

On the other hand, at the position in the B-B cross section in FIG. 4, the sheath fluid flows so as to push the sample against the second plate 131 from above, and the sample is crushed by the sheath fluid to thinly spread. Consequently, at the position in the B-B cross section in FIG. 4, the material components in the sample do not spread in the Z-axis direction, and the material components are easily brought into focus. Note that the sheath fluid and the sample fluid form laminar flows, and are scarcely mixed. This position in the B-B cross section is the position in the Y-axis direction suitable for the imaging of the material components, and hence the sample is imaged at this position in the Y-axis direction. This position is referred to as an imaging position, and the optical axis 110 of the objective lens 11A is set to this imaging position.

Note that the description has been made by using, as an example, the mode in which the sample having passed through the tapered section 138A of the flow cell 13A is in contact with the wall surface of the flow cell 13A. However, the structure of the flow cell and the flow of the sample are not limited only to this mode. For example, it is also possible to use the flow cell structured such that, after the sample passes through the tapered section 138A of the flow cell 13A, the sample is surrounded by the sheath fluid, and is thinly spread at the center of the sheath fluid.

Returning to FIG. 1, the first variable mechanism 22A changes the optical path length (hereinafter also referred to as a first optical path length) from the imaging lens 11B to the imaging surface of the first camera 23A, the second variable mechanism 22B changes the optical path length (hereinafter also referred to as a second optical path length) from the imaging lens 11B to the imaging surface of the second camera 23B, and the third variable mechanism 22C changes the optical path length (hereinafter also referred to as a third optical path length) from the imaging lens 11B to the imaging surface of the third camera 23C. Note that the distance from the imaging lens 11B is a distance from a front end portion, a rear end portion, or a center portion of the imaging lens 11B. The same applies to the objective lens 11A. The optical path length from the objective lens 11A to the imaging lens 11B is field.

Note that the imaging unit 1 may not include the imaging lens 11B. In that case, the first variable mechanism 22A changes the optical path length from the objective lens 11A to the imaging surface of the first camera 23A, the second variable mechanism 22B changes the optical path length from the objective lens 11A to the imaging surface of the second camera 23B, and the third variable mechanism 22C changes the optical path length from the objective lens 11A to the imaging surface of the third camera 23C.

Figure 5:
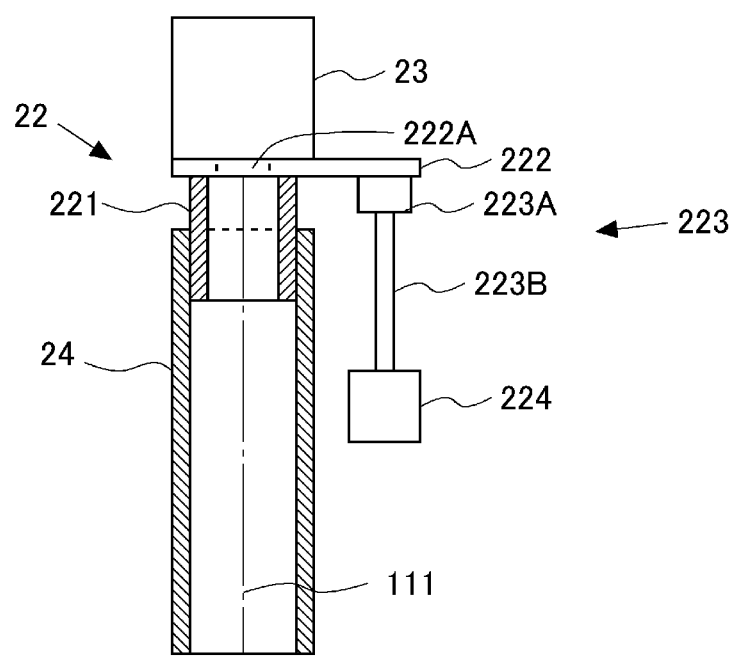
FIG. 5 is a view showing the schematic structure of a variable mechanism.

FIG. 5 is a view showing the schematic structure of the variable mechanism 22. The variable mechanism 22 includes a movable section 221, a seat 222, a feed screw 223, and a motor 224. The movable section 221 is formed to be cylindrical and is inserted in the lens barrel 24 so as to be able to advance or retreat. The central axis of the lens barrel 24 and the central axis of the movable section 221 are on the optical axis 111. The movable section 221 is fixed on one surface of the plate-like seat 222 and the camera 23 is fixed on the other side of the seat 222. A hole 222A is formed in the seat 222 at the mounting position of the camera 23, and the hole 222A is formed so that the light that has passed through the seat 222 enters the camera 23.

A nut 223A of the feed screw 223 is fixed on one surface of the seat 222, and a screw shaft 223B is fitted in the nut 223A. The axial direction of the screw shaft 223B is parallel to the direction of the optical axis 111. The screw shaft 223B is connected to the motor 224, and the screw shaft 223B rotates by rotating the motor 224. The rotation of the motor 224 is controlled by the CPU 14A. The motor 224 is fixed so as not to relatively move with respect to the lens barrel 24, and the nut 223A moves in the axial direction of the screw shaft 223B when the screw shaft 223B rotates. The movement distance at this time is determined depending on the angle of rotation of the screw shaft 223B and the pitch of the screw. The optical path length from the imaging lens 11B to the camera is changed by moving the movable section 221, the seat 222, and the camera 23 in the axial direction of the screw shaft 223B, that is, the direction of the optical axis 111 by the movement of the nut 223A. Note that means for changing the optical path length from the imaging lens 11B to the camera 23 is not limited to the abovementioned configuration. For example, the optical path length from the imaging lens 11B to the camera 23 may be changed by manually rotating the screw shaft 223B by the user.

Note that the first imaging section 10A, the second imaging section 10B, and the third imaging section 10C all include the variable mechanism 22 in the abovementioned description, but the imaging section 10 without the variable mechanism 22 is also possible. In that case, the optical path length from the imaging lens 11B to the camera 23 in the imaging section 10 without the variable mechanism 22 is fixed, and hence the optical path length from the imaging lens 11B to the camera 23 in other imaging sections 10 including the variable mechanism 22 only needs to be changed on the basis of the fixed optical path length.

Figure 6:
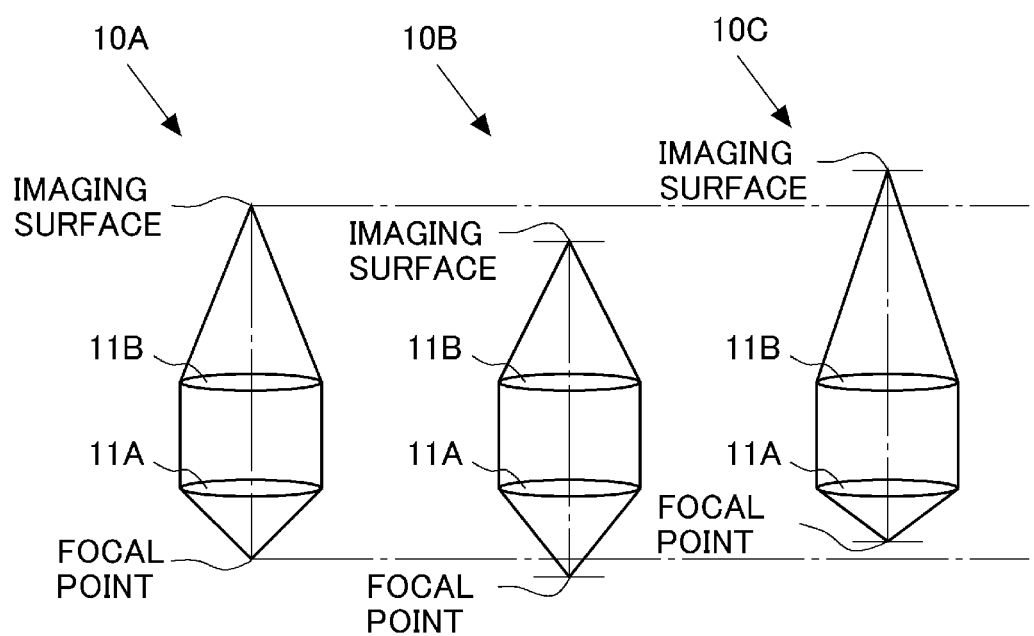
FIG. 6 is a view showing the relationship between the positions of imaging surfaces and focal points of cameras.

FIG. 6 is a view showing the relationship between the positions of the imaging surfaces and the focal points of the cameras 23. Starting from the left, the relationship in the first imaging section 10A, the second imaging section 10B, and the third imaging section 10C is shown. When the optical path length from the imaging lens 11B to the imaging surface becomes shorter, the optical path length from the objective lens 11A to the focal point on the object side becomes longer. When the optical path length from the imaging lens 11B to the imaging surface becomes longer, the optical path length from the objective lens 11A to the focal point on the object side becomes shorter. As described above, the optical path length from the imaging lens 11B to the imaging surface and the optical path length from the objective lens 11A to the focal point on the object side are correlated with each other. Note that the focus or the focal point hereinafter mean the focus or the focal point on the object side unless otherwise noted. Note that, when the imaging lens 11B is absent, the optical path length between the objective lens 11A and the focal point on the object side becomes shorter as the optical path length between the objective lens 11A and the imaging surface becomes longer.

For example, the CPU 14A operates the second variable mechanism 22B so that the second optical path length becomes shorter than the first optical path length by using the first optical path length as a reference. In addition, the CPU 14A operates the third variable mechanism 22C so that the third optical path length becomes longer than the first optical path length. By using the first optical path length as a reference, the first optical path length set by the first variable mechanism 22A is fixed and is not changed (The first variable mechanism 22A is unnecessary in that case.). The focal point according to the second imaging section 10B is on the far side than the focal point according to the first imaging section 10A in the direction of the optical axis 110 (on the side that is far from the objective lens 11A), and the focal point according to the third imaging section 10C is on the near side than the focal point according to the first imaging section 10A in the direction of the optical axis 110 (on the side that is near to the objective lens 11A).

The CPU 14A changes the deviation amount between the focal points of the imaging sections 10 in accordance with the analysis mode. A first mode and a second mode are provided for the analysis mode. Note that, three or more modes may be provided. The CPU 14A switches between the first mode and the second mode in accordance with the operation of the operation unit 17 by the user or a program stored in the ROM 14B. At this point, the deviation amount between the focal points of the imaging sections 10 is changed in accordance with, e.g., the size of the material component to be analyzed. By obtaining the relationship between the deviation amount between the focal points and the angle of rotation of the motors 224 in the variable mechanisms 22 in advance and storing the relationship in the ROM 14B, the deviation amount between the focal points can be changed to a desired deviation amount by rotating the motors 224 by the CPU 14A on the basis of the relationship. In the description below, the focal points are adjusted so that the deviation amount of the focal point of the second imaging section 10B from, the focal point of the first imaging section 10A and the deviation amount of the focal point of the third imaging section 10C from, the focal point of the first imaging section 10A are the same, but the deviation amounts of the focal points may be different. The first mode and the second mode are described below.

First Mode

In the first mode, the deviation amount between the focal points of the imaging sections 10 (the cameras 23) is changed so that the same material component can be imaged by the plurality of imaging sections 10, and the material component is analyzed on the basis of the images captured in that state. In the first mode, the CPU 14A adjusts the deviation amount between the focal points of the imaging section 10 so that the deviation amount (first deviation amount) between the focal points of the imaging sections 10 becomes smaller than the size of the material component to be analyzed. The maximum value of the width or the thickness of the material component maybe set as the size of the material component or the mean value of the width or the thickness of the material component may be set as the size of the material component. Note that, when the urine sample is used, the abovementioned deviation amount between the focal points is adjusted to, e.g., less than 10 μm and preferably adjusted to, e.g., from 1.5 μm to 5 μm in consideration of the size of the material component included in the urine sample. The typical sizes of the material components included in the urine sample are as below.

Erythrocyte: 8 μm or less, thickness is 2 μm or less
Leukocyte: a spherical shape that is from 12 μm to 15 μm (neutrophil)
Squamous epithelium (surface type): from 60 μm to 100 μm, thickness is from 3 μm to 5 μm
Squamous epithelium (medium, deep type): from 20 μm to 70 μm, thickness is 5 μm or more
Cast: various sizes exist
*Bacterium: bacterium* is 1 μm or less, fungus is from 3 μm to 6 μm Note that the deviation amount between the focal points of the imaging sections 10 is adjusted so that the second imaging section 10B and the third imaging section 10C are focused on different positions of the same material component given that the first imaging section 10A is focused on the center of the material component to be analyzed, for example.

For example, the deviation amount (first deviation amount) between the focal points of the imaging sections 10 may be adjusted so that the depth of field of the image captured by the second imaging section 10B and the depth of field of the image captured by the first imaging section 10A partially overlap with each other and the depth of field of the image captured by the third imaging section 100 and the depth of field of the image captured by the first imaging section 10A partially overlap with each other. Note that there are cases where even a material component that is in a position slightly out of the depth of field can be analyzed from the image. A range obtained by further adding a predetermined margin to the depth of field may be defined as an imaging range, and the deviation amount between the focal points of the imaging sections 10 may be adjusted so that the imaging ranges of the images partially overlap with each other.

Figure 7:
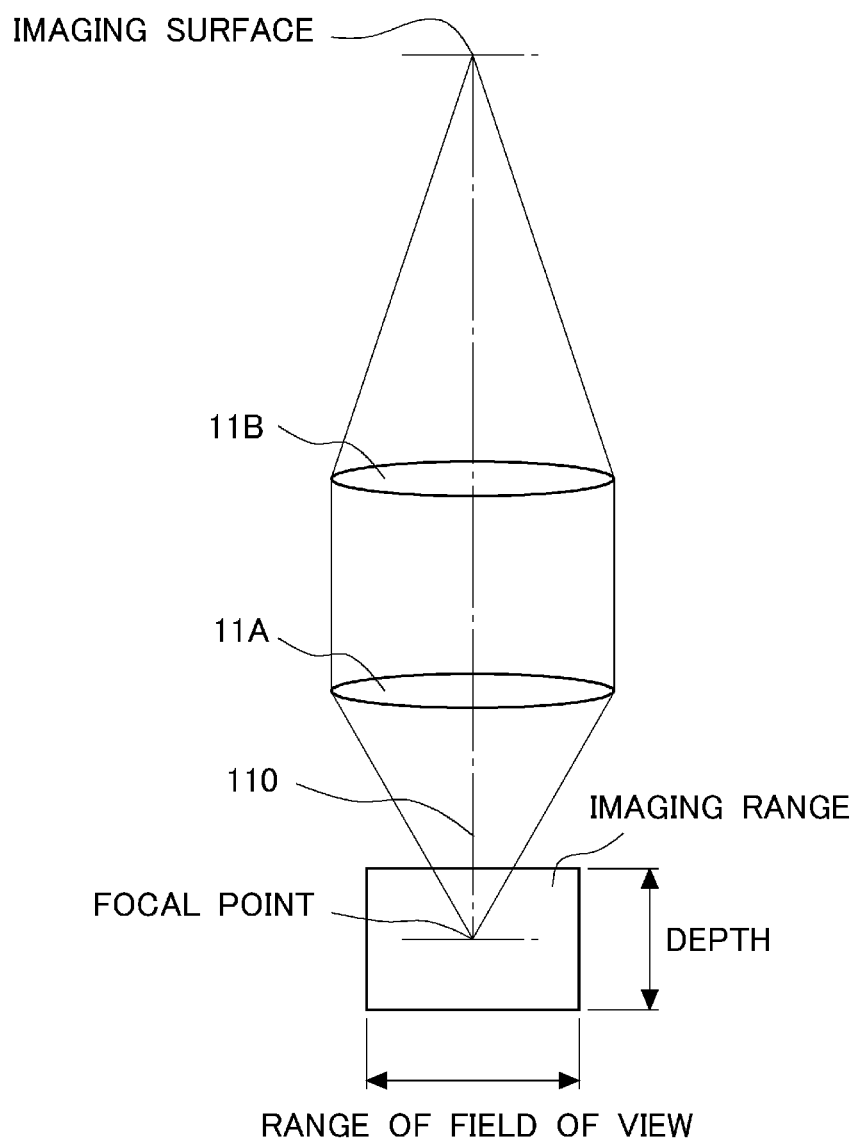
FIG. 7 is a view for describing an imaging range.

FIG. 7 is a view for describing an imaging range. The imaging range is a range in which the material component can be analyzed or the material component can be extracted by the image captured by the imaging section 10 and is a range determined from the range of field of view of the camera 23 and the depth in which the material component can be extracted. The range of field of view of the camera 23 is determined by the size of the imaging surface and the magnification of an optical system according to the image. The depth in which the material component can be extracted is a range obtained by adding a predetermined margin to the depth of field. Note that the predetermined margin is preset as a range in which the material component can be analyzed or a range in which the material component can be extracted.

Figure 8:
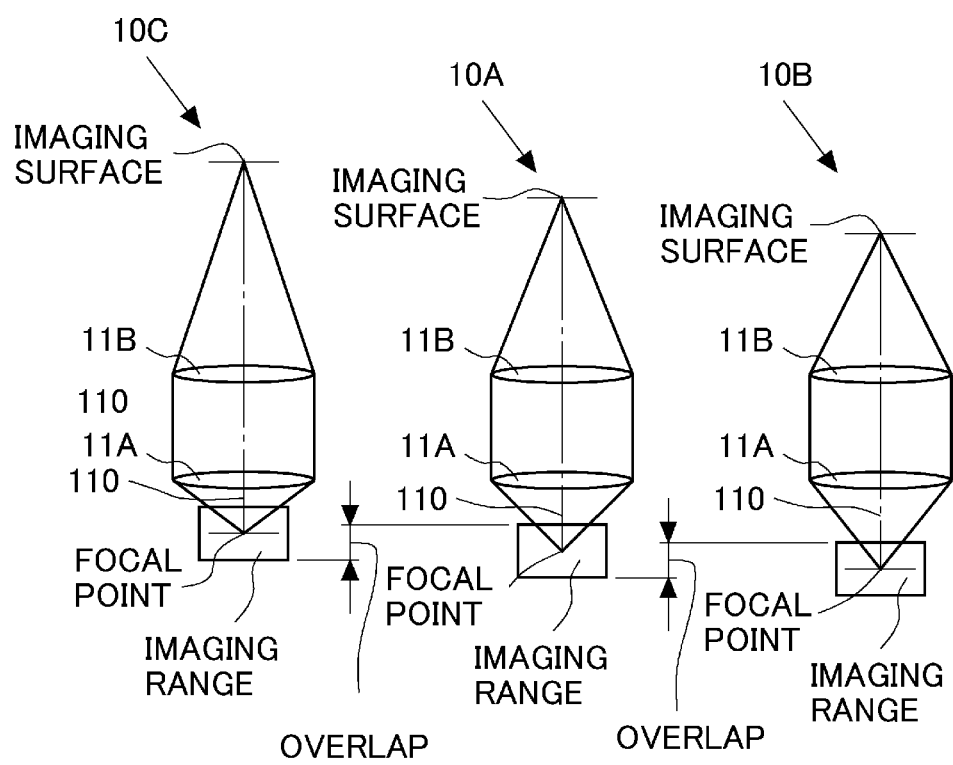
FIG. 8 is a view showing the relationship between imaging ranges of imaging sections when the deviation amount between the focal points of the imaging sections is adjusted so that the imaging ranges partially overlap with each other.

FIG. 8 is a view showing the relationship between the imaging ranges of the imaging sections 10 when the deviation amount between the focal points is adjusted so that the imaging ranges of the imaging sections 10 partially overlap with each other. Starting from the left, the relationship in the third imaging section 10C, the first imaging section 10A, and the second imaging section 10B is shown. When the focal point is adjusted by changing the optical path length from the imaging lens 11B to the imaging surface of the camera 23, the imaging range is shifted in accordance with the adjustment of the focal point. In the state shown in FIG. 8, the imaging range of the third imaging section 105 and the imaging range of the first imaging section 10A partially overlap with each other and the imaging range of the first imaging section 10A and the imaging range of the second imaging section 10B partially overlap with each other in ranges indicated as "OVERLAP".

Note that the deviation amount between the focal points of the imaging sections 10 tends to become smaller than the size of the material component when the focal points of the imaging sections 10 are adjusted so that the imaging ranges partially overlap with each other as shown in FIG. 8, although it depends on the material component to be analyzed.

The CPU 14A causes the first imaging section 10A, the second imaging section 10B, and the third imaging section 10C to simultaneously capture the same images having the common optical axis 110 after adjusting the deviation amount between the focal points of the imaging sections 10. Hereinafter, the image captured by the first imaging section 10A is also referred to as a first image, the image captured by the second imaging section 10B is also referred to as a second image, and the image captured by the third imaging section 10C is also referred to as a third image.

Specifically, the first camera 23A, the second camera 23B, and the third camera 23C simultaneously capture still images of the material component in the sample that flows in the flow cell 13A. The imaging is magnification imaging, and the lighting time of the light source 12 and the imaging time (exposure time) of each of the first camera 23A, the second camera 23B, and the third camera 23C are synchronized by the controller 14. Parallel light enters the flow cell 13A from the light source 12. In the imaging, the light source 12 is lighted once or multiple times. The lighting time of the light source 12 depends on the speed of flow of the sample and is set so that a motion blur falls within a permissible range. When the light source 12 is caused to emit light a plurality of times in one exposure, the number of material components included in one image is increased, and hence it is possible to further increase the accuracy in the analysis of the material component. The blinking timing of the light source 12 in this case is determined in consideration of the relationship between the speed of flow of the sample and the lighting time of the light source 12 such that the same sample is not imaged. A plurality of images described above may be captured by the cameras 23.

For example, the CPU 14A grasps the positions, sizes, and number of the material components from the first image, determines a cut-out size of an image from the grasped size of the material component, and generates a cut-out image. The cut-out image generated from the first image is hereinafter also referred to as a first cut-out image. The first cut-out image is an image obtained by comparing a background image with the captured image, surrounding a part having a difference by using a square, and cutting out an image in the square.

Prior to the generation of the first cut-out image, the CPU 14A creates an image obtained by averaging pixel values of individual pixels as a background image for each first image by using stored data of the first image. The pixel value may be the brightness or RGB values of each pixel. The CPU 14A executes a program (cut-out process) stored in the ROM 14B, and the first cut-out image is thereby generated. The first cut-out image is stored in the RAM 14C together with its cut-out position and cut-out size. For example, the CPU 14A generates the first cut-out image for each of the material components included in the first captured image.

The CPU 14A generates a cut-out image also for the second image by cutting out a material component from a position corresponding to the first cut-out image (specifically, a position in which the X-axis and Y-axis coordinates are the same). The CPU 14A generates a cut-out image also for the third image by cutting out a material component from a position corresponding to the first out-out image. Hereinafter, the cut-out image generated from, the second image is also referred to as a second cut-out image and the cut-out image generated from the third image is also referred to as a third cut-out image.

The CPU 14A stores the first cut-out image, the second cut-out image, and the third cut-out image cut out from the same positions in the first image, the second image, and the third image in a RAM 14C in association with each other. The first cut-out image, the second cut-out image, and the third out-out image are used in various analyses by the CPU 14A. As a result, an action similar to that in which an observer observes a material component by manually changing the focal point when visual confirmation observation is performed through a microscope can be realized also in continuous image photographing using the flow cell.

Figure 9:
FIG. 9 is a picture substituting for a figure showing cut-out images of material components classified into leukocytes as an example.

FIG. 9 is a view showing cut-out images of material components classified into leukocytes as an example. Note that material components other than leukocytes are also targets to be analyzed. The third cut-out images, the first out-out images, and the second cut-out images are shown starting from the top, and images obtained by cutting out the same material component (the same individual) are horizontally arranged. As described above, the cut-out images are stored in the RAM 14C in association with each other. In other words, the images of the material component that is the same individual are arranged in order from the image of which optical path length from the objective lens 11A to the focal point is the shortest or the longest (one is in ascending order and the other is in descending order).

The CPU 14A analyzes (identifies) the material components by comparing the feature amounts of the cut-out images and the feature amount for each material component pre-stored in the ROM 14B with each other. Examples of the feature amounts can include colors, shapes, and sizes. If only one imaging section 10 is provided, only an image of the material component that is out of focus can be acquired when the material component is in a position out of focus of the imaging section 10. Therefore, there is a fear that an appropriate feature amount cannot be acquired from the captured image and the CPU 14A cannot distinguish the type of the material component. When the material component is indistinguishable, the user needs to perform observation by visual confirmation by using a microscope in order to identify the material component.

On the other hand, feature amounts sufficient to distinguish the type of the material component from one of the images having different focal points can be acquired, the indistinguishable rate can be reduced, and the number of times of performing observation by visual confirmation by the user can be reduced by simultaneously acquiring a plurality of images of which focal points are shifted from each other by using the plurality of imaging sections 10.

In addition, the same material component (same individual) is imaged by the plurality of imaging sections 10 having different focal points, and hence the information volume that can be acquired from the same material component is increased. Therefore, the accuracy in the analysis of the material component can be further increased. By switching and displaying the cut-out images obtained by extracting the same material component as shown in FIG. 9 on the same position on the display unit 16 in order from the cut-out image of which focal point is on the far side (that is, in order of the second cut-out image, the first cut-out image, and the third cut-out image, and in order from the bottom in FIG. 9) or in order from the cut-out image of which focal point is on the near side (that is, in order of the third cut-out image, the first cut-out image, and the second cut-out image, and in order from the top in FIG. 9), the cut-out images can be switched by the same visual performance as the observation where the user manually shifts the focus of the microscope. Therefore, the material component is easily identified even when the user identifies the material component by referring to the display unit 16 by himself or herself. The time and effort of the test can be reduced as compared to the microscope is used.

For example, even when the identification cannot be performed with one cut-out image, the identification can become easier by switching and displaying other cut-out images because the identification can be performed in consideration of the information included in the other cut-out images. In addition, the user can check whether the identification is accurately performed by switching and displaying the cut-out images for the material component identified by the CPU 14A. Note that the cut-out images may be automatically switched by the CPU 14A or manually switched by the user by using, e.g., a mouse. The identification may be performed by displaying the first cut-out image, the second cut-out image, and the third cut-out image so as to overlap with each other in the same position. Even in that case, the information included in the cut-out images can be seen at once, and hence the identification may become easier. As shown in FIG. 9, the first cut-out image, the second cut-out image, and the third cut-out image may be displayed in parallel with each other in different positions.

A typical microscope has a depth of field shallow for the size of the material component, and hence it may be difficult to grasp the entire material component at once. In that case, the entire material component is grasped by manually adjusting the focal point by the user. On the other hand, when the focal points of the imaging sections 10 are adjusted so that the deviation amount between the focal points of the imaging sections 10 becomes smaller than the size of the material component to be analyzed, a plurality of images of which focal points are shifted from each other can be acquired for the material component that is the same individual. Then, images having different focal points can be observed also in continuous measurement using the flow cell by successively switching and displaying the plurality of acquired images.

The CPU 14A can also count the number of the material components on the basis of the number of the cut-out images. In the first mode, an image captured by one imaging section 10 (for example, the first imaging section 10A) is used when the number of the material components are counted.

The CPU 14A identifies the material component by comparing, e.g., the feature amount of the first cut-out image and the feature amount for each material component pre-stored in the ROM 14B. The material component that was not able to be identified is identified on the basis of the corresponding second cut-out image. That is, the material component is identified by comparing the feature amount of the second cut-out image and the feature amount of the material component pre-stored in the ROM 14B with each other. Identification based on the third cut-out image is similarly attempted for the material component that was not able to be identified even after the abovementioned identification. As described above, the number of the material components that need to be observed by the visual confirmation by the user for identification can be reduced by attempting the identification a plurality of times on the basis of the plurality of image having different focal points.

Note that the identification method for the material component is not limited to the method above, and the material component may be identified by determining the feature amounts acquired from the first cut-out image, the second cut-out image, and the third cut-out image in a comprehensive manner. The identification an that case is also performed an accordance with a program stored in the ROM 14B.

Figure 10:
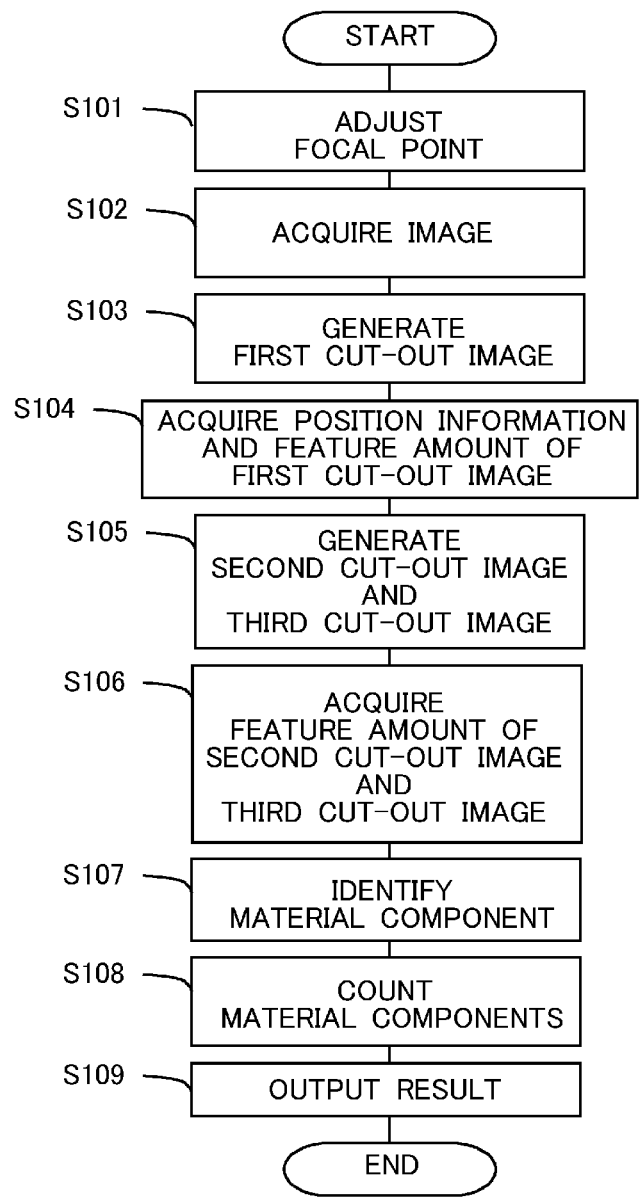
FIG. 10 is a flowchart showing a procedure for identifying the material components in a first mode.

FIG. 10 is a flowchart showing a procedure for identifying the material components in the first mode. The present flowchart is executed by the CPU 14A.

In Step S101, the CPU 14A adjusts the focal points of the imaging sections 10 by operating the variable mechanisms 22. At this point, the focal points of the imaging sections 10 are adjusted so that the deviation amount between the focal points of the imaging sections 10 becomes smaller than the size of the material component. At this point, the focal points of the imaging sections 10 are adjusted so that the imaging ranges of the imaging sections 10 partially overlap with each other.

In Step S102, the CPU 14A acquires the images captured by the first imaging section 10A, the second imaging section 10B, and the third imaging section 10C.

When the process in Step S102 is completed, the procedure proceeds to Step S103 in which the CPU 14A cuts out the material component from the first image to generate the first cut-out image, and causes the RAM 14C to store the first cut-out image. The first cut-out image is generated by the number of the material components imaged in the first image.

When the process in Step S103 is completed, the procedure proceeds to Step S104 in which the CPU 14A acquires the position information and the feature amount of the first cut-out image. The position information and the feature amount of the first cut-out image are stored in the RAM 14C in association with the first cut-out image. A program pre-stored in the ROM 14B is used for the acquisition of the feature amount.

When the process in Step S104 is completed, the procedure proceeds to Step S105 in which the CPU 14A cuts out the material component from the second image and the third image and generates the second cut-out image and the third cut-out image. The second cut-out image and the third cut-out image are generated by cutting out the material component in the same position as the first cut-out image on the basis of the position information of the plurality of first cut-out images. The second cut-out image and the third cut-out image obtained by cutting out the same position as the first cut-out image are stored in the RAM 14C in as with the first cut-out image.

When the process in Step S105 is completed, the procedure proceeds to Step S106 in which the CPU 14A acquires the feature amounts of the second cut-out image and the third cut-out image. The feature amounts of the second cut-out image and the third cut-out image are stored in the RAM 14C.

When the process in Step S106 is completed, the procedure proceeds to Step S107 in which the CPU 14A identifies the material component on the basis of the feature amounts of the cut-out images acquired in Step S104 and Step S106. A program pre-stored in the ROM 14B s used for the identification. For example, the CPU 14A identifies the material component by comparing at least one of the feature amount of the first cut-out image, the feature amount of the second cut-out image, or the feature amount of the third cut-out image and the feature amount for each material component pre-stored in the ROM 14B. Note that the feature amount of the second cut-out image may be acquired before cutting out the third image in Step S105 and Step S106, for example, and the order of the steps in Step S105 and Step S106 is not particularly limited.

When the process in Step S107 is completed, the procedure proceeds to Step S108 in which the CPU 14A counts the material components for each type of the material component identified in Step S107, and the procedure then proceeds to Step S109 in which in the result of the count in Step S108 is output. The CPU 14A may perform various analyses on the basis of the result of the count. Note that, when there is a material component that cannot be identified in Step S107, a notification thereof is displayed on the display unit 16.

Thus, it is possible to determine the positions and number of the material components based on the first cut-out image, and increase the accuracy in the analysis of the material component by performing the analysis of the material components based on the first cut-out image, the second cut-out image, and the third cut-out image. In addition, when an image different from the first image, the second image, and the third image is acquired, the acquisition of the image requires only one light source 12, one objective lens 11A, and one imaging lens 11B.

When the material component cannot be identified because the feature amounts of the cut-out images do not match with the feature amount for each material component pre-stored in the ROM 14B in the abovementioned Step S107, the user performs the identification on the basis of the cut-out images according to the material components. At this point, the CPU 14A displays the cut-out images stored in the RAM 14C so that images are successively switched and displayed in the same position on the display unit 16 in order of the second cut-out image, the first cut-out image, and the third cut-out image or in order of the third cut-out image, the first cut-out image, and the second cut-out image. The timing of switching the cut-out images may be designated by the CPU 14A in accordance with the display time of the cut-out images stored in the ROM 14B or may be designated in accordance with the operation of the operation unit 17 by the user. When the user uses a scroll wheel of a mouse as the operation unit 17, the cut-out images may be switched in accordance with the rotation of the scroll wheel. When the user uses a keyboard as the operation unit 17, the cut-out images may be switched in accordance with any key that is pressed.

As described above, the accuracy in the analysis of the material component can be increased and the material component can be easily identified by adjusting the focal points of the imaging sections 10 so that the deviation amount between the focal points of the imaging sections 10 becomes smaller than the size of the material component to be analyzed in the first mode. As a result, the number of times the user observes the material component by visual confirmation can be reduced. Even if there is a material component that cannot be identified by the process of the CPU 14A, the number of times the user observes the material component by a microscope can be reduced because the cut-out images of the material component can be observed by being successively switched so as to shift the focal point.

Second Mode

In the second mode, the deviation amount (second amount) between the focal points of the imaging sections 10 (the cameras 23) on the object side is adjusted so that the material components distributed in the flow cell can be imaged in a wider range in the direction of the optical axis 110 of the objective lens 11A, and the number of the material components is mainly counted on the basis of the images captured in the state. Therefore, in the second mode, the deviation amount between the focal points of the imaging sections 10 on the object side is caused to be larger than the size of the material component to be analyzed. Note that, when the urine sample is used, the abovementioned deviation amount between the focal points is adjusted to, e.g., 10 μm or more in consideration of the size of the material component included in the urine sample.

Figure 11:
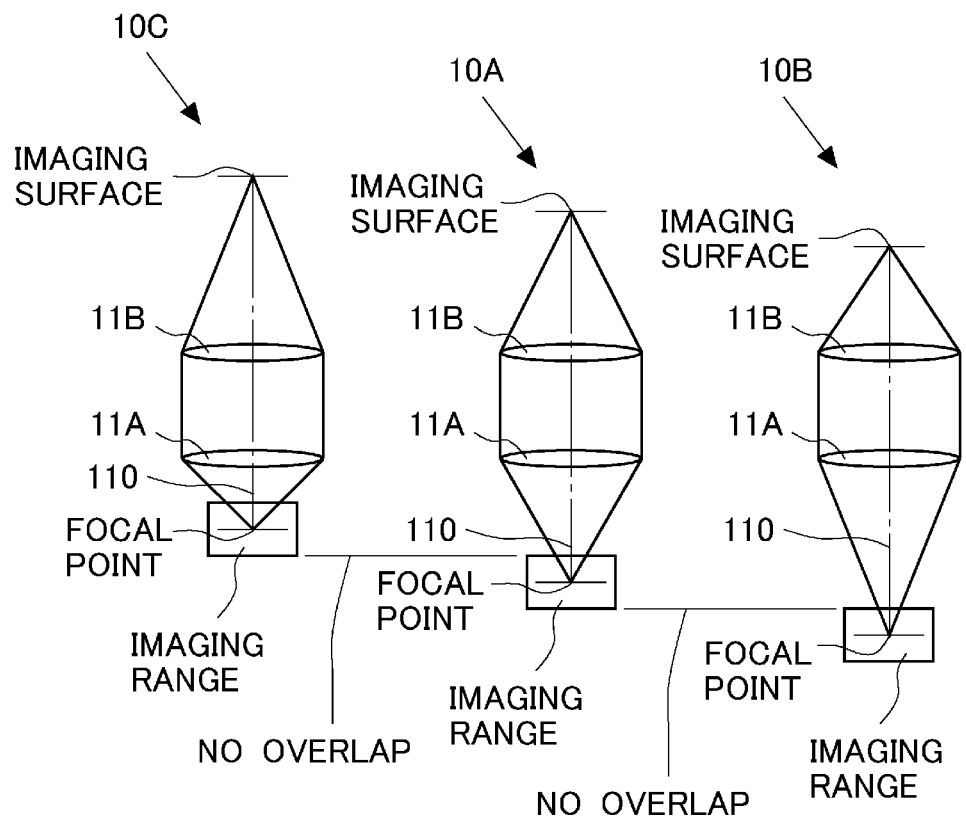
FIG. 11 is a view showing the relationship between the imaging ranges of the imaging sections when the deviation amount between the focal points of the imaging sections are adjusted so that the imaging ranges do not overlap with each other.

FIG. 11 is a view showing the relationship between the imaging ranges of the imaging sections 10 when the deviation amount between the focal points of the imaging sections 10 is adjusted so that the imaging ranges do not overlap with each other. Starting from the left, the relationship in the third imaging section 10C, the first imaging section 10A, and the second imaging section 10B is shown. The imaging range of the first imaging section 10A is on the far side (the position far from the objective lens 11A) of the fourth flow path 138 than the imaging range of the third imaging section 10C in the direction of the optical axis 110, and the imaging ranges do not overlap with each other. The imaging range of the second imaging section 10B is on the far side than the imaging range of the first imaging section 10A in the direction of the optical axis 110, and the imaging ranges do not overlap with each other. The imaging ranges may be adjacent or separated.

Note that the deviation amount between the focal points of the imaging sections 10 becomes larger than the size of the material component when the focal points of the imaging sections 10 are adjusted so that the imaging ranges do not overlap with each other as shown in FIG. 11, although it depends on the material component to be analyzed.

The thickness of the imaging ranges of the imaging sections 10 in the direction of the optical axis 110 of the objective lens 11A is thinner than the thickness of the sample flowing through the flow cell 13A. Therefore, if the sample is imaged by one imaging section 10, there are ranges that cannot be imaged and the material component on the near side or the far side of the imaging range in the direction of the optical axis 110 cannot be imaged. In that case, analysis based on the number of the material components included in the captured image can be conceived, for example, under the assumption that the number of the material components per unit volume of the sample is the same for any place in the sample.

However, the distribution of the material components may be concentrated on one side in the sample flowing through the flow cell 13A. As a result, the number of the material components per unit volume of the sample is not uniform, and hence the number of the imaged material components differ depending on the focal point when the material components are imaged. Then, there is a fear that the results of the analysis differ depending on the focal point. As described above, when analysis based on the number of the material components in the sample is performed, the accuracy of the analysis decreases if the number of the material components included in the captured image and the total number of the material components included in the sample are not correlated with each other.

On the other hand, the analysis apparatus 20 includes the plurality of imaging sections 10, and hence the material components included in a wider range can be imaged by shifting the focal points according to the imaging sections 10 in the direction (Z-axis direction) of the optical axis 110 of the objective lens 11A. In the second mode, the deviation amount (second amount) between the focal points of the imaging sections 10 on the object side is adjusted so that the imaging ranges of the imaging sections 10 do not overlap with each other. That is, the deviation amount between the focal points is adjusted as the second amount so that the deviation amount between the focal points of the imaging sections 10 becomes larger than the size of the material component to be analyzed. As a result, the deviation amount (second amount) in the second mode becomes larger than the deviation amount (first amount) in the first mode. The material components in imaging ranges that are different (not overlapping) in the direction of the optical axis 110 are imaged in the first image, the second image, and the third image acquired by adjusting the focal points as described above. Therefore, the correlation between the number of the material components included in the captured first image, the captured second image, and the captured third image and the total number of the material components included in the sample is increased, and hence the accuracy in the analysis can be increased.

Note that, even when the material components are out of the depth of field and the image is out of focus, the number of the material components can be counted if the presence of the material components can be grasped, and hence the deviation amount between the focal points may be adjusted so that the material components do not overlap with each other within the range in which the material components can be checked. The first mode and the second mode are used for different purposes, and hence the optimum imaging ranges are set depending on the purposes thereof. In the second mode, the deviation amount between the focal points may be adjusted so that the depths of field of the images simply do not overlap with each other. The focal points are adjusted by operating the variable mechanisms 22 by the CPU 14A.

The CPU 14A generates the first cut-out images, the second cut-out images, and the third cut-out images, and counts the total number of the cut-out images as the number of the material components. Note that the number of the material components may be counted by comparing the first image, the second image, and the third image and backgound images corresponding to those images with each other, considering that places where there are differences are places where there are material components, and counting those places. The number of the material components acquired as described above is stored in the RAM 14C and used in various analyses by the CPU 14A.

An oversight in counting the material components can be suppressed (accuracy in the count of the material component can be increased) because the ranges imaged by the imaging sections 10 do not overlap with each other and the sample can be imaged in a wider range. As a result, the accuracy in the analysis based on the number of the material components can be increased.

Figure 12:
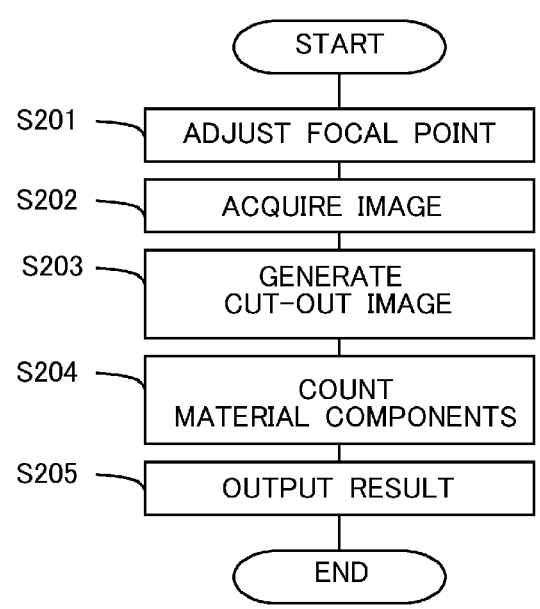
FIG. 12 is a flowchart showing a procedure for identifying the material components in a second mode.

FIG. 12 is a flowchart showing a procedure for identifying the material components in the second mode. The present flowchart is executed by the CPU 14A.

In Step S201, the CPU 14A adjusts the focal points of the imaging sections 10 by operating the variable mechanisms 22. At this point, the focal points of the imaging sections 10 are adjusted so that the deviation amount between the focal points of the imaging sections 10 becomes larger than the size of the material component, for example.

In Step S202, the CPU 14A acquires the first image, the second image, and the third image. When the process in Step S202 is completed, the procedure proceeds to Step S203 in which the CPU 14A cuts out the material components from the first image, the second image, and the third image, generates the first cut-out image, the second cut-out image, and the third cut-out image, and stores the cut-out images in the RAM 14C.

When the process in Step S203 is completed, the procedure proceeds to Step S204 in which the CPU 14A calculates the total number of the first cut-out images, the second cut-out images, and the third cut-out images. The total value corresponds to the number of the material components. The CPU 14A stores the total value in the RAM 14C. When the process in Step S204 is completed, the procedure proceeds to Step S205 in which the CPU 14A outputs the result of the count in Step S204. The CPU 14A may perform various analyses on the basis of the result of the count.

As described above, in the second mode, the number of the material components can be accurately counted by adjusting the focal points of the imaging sections 10 so that the deviation amount between the focal points of the imaging sections 10 becomes larger than the size of the material component to be analyzed.

Switching Process of Analysis Modes

Figure 13:
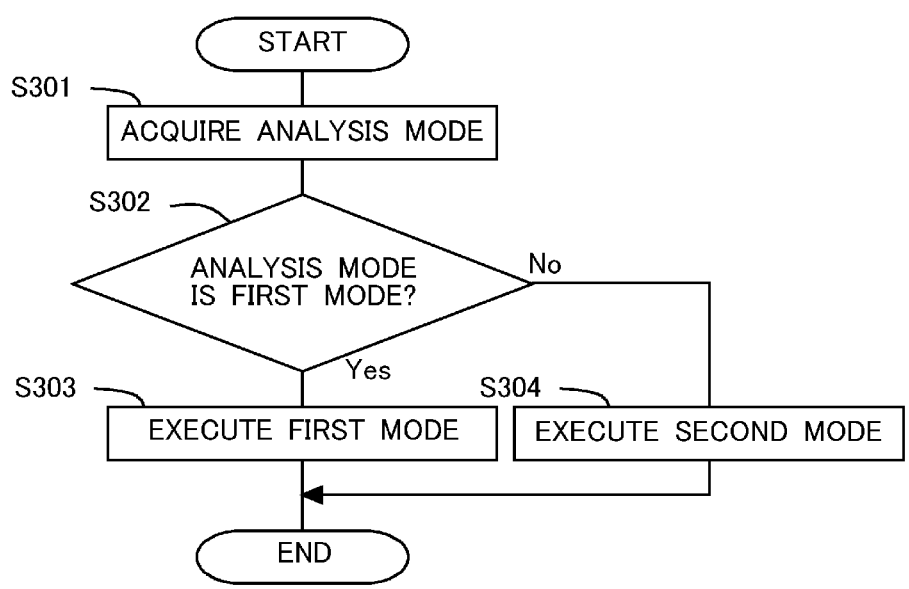
FIG. 13 is a flowchart showing a procedure of a switching control of the focal points.

The analysis modes are switched in accordance with a flowchart below shown n FIG. 13. FIG. 13 is a flowchart showing a procedure of a switching control of the focal points. The flowchart shown in FIG. 13 is executed by the CPU 14A.

In Step S301, the CPU 14A acquires the analysis mode set by the user. For example, the first mode and the second mode can be switched by operating the operation unit 17 by the user. Therefore, the CPU 14A acquires the analysis mode set by the user by acquiring the operate state of the operation unit 17.

When the process in Step S301 is completed, the procedure proceeds to Step S302 in which the CPU 14A determines whether the analysis mode set by the user is the first mode. When the determination in Step S302 is YES, the procedure proceeds to Step S303 in which the CPU 14A analyzes the material component in the first mode. At this point, the flowchart shown in FIG. 10 is executed.

On the other hand, when the determination in Step S302 is NO, the procedure proceeds to Step S304 in which the CPU 14A analyzes the material component in the second mode. At this point, the flowchart shown in FIG. 12 is executed. As described above, the material component can be analyzed in different modes by performing imaging by switching the focal points according to the imaging sections 10 in accordance with the analysis mode desired by the user.

Other Embodiments

In the abovementioned embodiment, at least a part of the imaging section 10 includes the variable mechanisms 22, but instead, all of the imaging sections 10 do not necessarily need to include the variable mechanisms 22. In that case, the user cannot change the focal points of the imaging sections 10. For example, the camera 23 is fixed to an end portion of the lens barrel 24. As a result, the first optical path length, the second optical path length, and the third optical path length are fixed. At this time, the first optical path length, the second optical path length, and the third optical path length are adjusted in advance so that the focal points of the imaging sections 10 in the flow cell 13A are (different from each other. The imaging ranges and the focal points of the imaging sections 10 in this case may correspond to either of the first mode or the second mode described in the abovementioned embodiment. The CPU 14A simultaneously captures the images having the common optical axis 110 by the first imaging section 10A, the second imaging section 10B, and the third imaging section 10C. The same methods as those in the first mode or the second mode can be used for the imaging method and the method for the processing thereafter.

There are three imaging sections 10 in the abovementioned embodiment, but the number of the imaging sections 10 is not limited thereto and may be two or four or more. The accuracy in the analysis of the material component can be increased as the number of the imaging sections 10 increases, and hence the number of the imaging sections 10 may be designated in accordance with the required accuracy in the analysis.

The switching of the analysis modes can be applied to both of a finite correction optical system and an infinity correction optical system. The imaging lens 11B is not an essential configuration.

When the optical path lengths of the imaging sections 10 are adjusted, the optical path lengths may be changed by inserting optical elements having different thicknesses in the optical paths without physically changing the distances.

Other modes in which the focal points of the imaging sections 10 are different from the first mode and the second mode can be further combined other than those modes. The imaging does not necessarily need to be performed by using all the imaging sections 10, and the imaging may be performed by using a part of the imaging sections 10. When the material components to be analyzed are concentrated on one side in the sample in the direction of the optical axis 110, the material components may be analyzed by grasping places where the number of the material components to be analyzed is relatively high by executing the second mode, and then executing the first mode by bringing the focal point of the first imaging section 10A on the place.

The invention claimed is:

1. An analysis apparatus, comprising:
a flow cell including a flow path through which a sample fluid containing a material component and a sheath fluid flow;
a light source;
a branch section configured to cause light emitting from the light source and passing through the sample containing the material component to branch off into a plurality of optical paths;
a plurality of imaging devices for simultaneously capturing images at different focal points on an optical axis in the flow path by using the light caused to branch off into the plurality of optical paths; and
a controller configured to process the captured images, wherein
the flow cell includes a sample fluid supply port which supplies the sample fluid to the flow path, a sheath fluid supply port which supplies the sheath fluid to the flow path, and a joining section joining the flow path through which the sample fluid flows and the flow path through which the sheath fluid flows,
the flow path includes a flat section which is formed on a downstream side of the joining section and having a thinner thickness than the joining section, and a tapered section connecting the joining section and the flat section,
the sample fluid forms laminar flow thinner than the thickness of the sample fluid supply port at the flat section, and
the light from the light source is emitted to the flat section, and the focal points on the optical axis of the plurality of imaging devices are different in position in the thickness direction of the flow cell.

2. The analysis apparatus according to claim 1, wherein the branch section is a beam splitter.

3. The analysis apparatus according to claim 1, further comprising at least one variable mechanism configured to change the focal point on the optical axis of the imaging device.

4. The analysis apparatus according to claim 3, wherein the variable mechanism is further configured to change optical path lengths between imaging lens corresponding to the imaging device and imaging surface of the imaging device or optical path lengths between objective lens corresponding to the imaging device and the imaging surface of the imaging device.

5. The analysis apparatus according to claim 3, wherein the plurality of imaging devices include three cameras, and
the light caused to branch by the branch section enters at least two cameras out of the three cameras via the variable mechanism.

6. The analysis apparatus according to claim 3, wherein the analysis apparatus includes a first mode and a second mode that are analysis modes,
the variable mechanism is further configured to change the focal point on the optical axis of the imaging device depending on the first mode and the second mode, and
a deviation amount between the focal point of the imaging device in the first mode is smaller than a deviation amount between the focal point of the imaging device in the second mode.

7. The analysis apparatus according to claim 6, wherein the variable mechanism is further configured to adjust the focal points such that ranges imaged by the plurality of imaging devices partially overlap with each other in the first mode.

8. The analysis apparatus according to claim 6, wherein the variable mechanism is further configured to adjust the focal points such that ranges imaged by the plurality of imaging devices do not overlap with each other in the second mode.

9. The analysis apparatus according to claim 6, further comprising a display unit, wherein
the controller is further configured to switch images of a same material component captured by the plurality of imaging devices between a descending order or an ascending order, based on the focal points and displays the images on the display unit in the first mode.

10. The analysis apparatus according to claim 1, wherein the plurality of imaging devices image ranges that partially overlap with each other.

11. The analysis apparatus according to claim 1, wherein the controller is further configured to cut out images in corresponding positions from the images captured by the plurality of imaging devices.

* * * * *